United States Patent [19]
Rao

[11] Patent Number: 5,463,152
[45] Date of Patent: Oct. 31, 1995

[54] HALOFLUOROCARBON HYDROGENOLYSIS

[75] Inventor: V N. Mallikarjuna Rao, Wilmington, Del.

[73] Assignee: E. I. Du Pont de Nemours and Company, Wilmington, Del.

[21] Appl. No.: 351,907

[22] Filed: Dec. 8, 1994

[51] Int. Cl.$^6$ .................................................. C07C 19/08
[52] U.S. Cl. .................................................. 570/176
[58] Field of Search .................................................. 570/176

[56] References Cited

U.S. PATENT DOCUMENTS

| | | | |
|---|---|---|---|
| 2,942,036 | 6/1960 | Smith et al. | 260/653 |
| 4,319,060 | 3/1982 | Cunningham et al. | 570/177 |
| 4,873,381 | 10/1989 | Kellner et al. | 570/176 |
| 4,996,379 | 2/1991 | Oshio et al. | 570/176 |
| 5,036,036 | 6/1991 | Lerou | 502/317 |
| 5,091,600 | 2/1992 | Moore et al. | 570/151 |
| 5,097,082 | 3/1992 | Anton | 570/176 |
| 5,171,901 | 12/1992 | Gassen et al. | 570/168 |
| 5,208,396 | 5/1993 | Anton | 570/176 |
| 5,364,991 | 11/1994 | Aoyama et al. | 570/176 |

FOREIGN PATENT DOCUMENTS

| | | |
|---|---|---|
| 1-319441 | 12/1989 | Japan. |
| 1578933 | 11/1980 | United Kingdom. |

WO94/20440 9/1994 WIPO.

OTHER PUBLICATIONS

Bitner, J. L. et al., "Thermochemical and Photochemical studies on organic fluorine compounds", *Chemical Abstracts*, 54:22311C. (1970).

Zubovich, I. A., "Oxidation–Reduction Catalysis by Palladium–Gold and Palladium—Silber Systems on Different Types of Carrier", *Russian Journal of Phys. Chem.*, 56(5), 798–799 (1982).

Sokolskii, D. V. et al., "Liquid–phase Hydrogenation of β–Ionone on a Stationary Ni–Cr$_2$O$_3$ Catalyst in a Flow Apparatus under Hydrogen Pressure", *Russian Journal of Phys. Chem.*, 56(7), 1075–1076 (1982).

Bitner, J. L. et al., *U.S. Dept. of Comm. Off. Tech. Serv./Report* 136732, pp. 25–27 (1958).

*Primary Examiner*—Alan Siegel

[57] ABSTRACT

A process is disclosed for the hydrogenolysis of a saturated acyclic starting material of the formula $C_nH_aX_bF_c$ (X is Cl and/or Br, n is 1 to 4, a 0 to 3, b is 1 to 4, and c is 1 to 9) which involves reacting the starting material with hydrogen at an elevated temperature of about 300° C. or less in the presence of a catalyst containing a catalytically effective amount of palladium supported on trivalent chromium oxide and in the presence of an acid of the formula HZ (Z is Cl, Br, and/or F) to produce a product compound of the formula $C_nH_dX_eF_f$ where e is less than b and d+e equals a+b.

10 Claims, No Drawings

HALOFLUOROCARBON HYDROGENOLYSIS

FIELD OF THE INVENTION

This invention relates to the catalytic hydrogenolysis of halofluorocarbons and hydrohalofluorocarbons, and more particularly, to the hydrogenolysis of said materials using palladium-containing catalysts.

BACKGROUND

The catalytic hydrogenolysis of chlorofluorocarbons and hydrochlorofluorocarbons is known in the art. For example, J. L. Bitner et al., (U.S. Dep. Comm. Off. Tech. Serv/Rep. 136732, (1958), pp. 25–27) have reported the hydrogenolysis of 1,2-dichlorotetrafluoroethane (i.e., $CClF_2CClF_2$ or CFC-114) to 1,1,2,2-tetrafluoroethane (i.e., $CHF_2CHF_2$ or HFC-134). British Patent Specification 1,578,933 illustrates that mixtures of $C_2Cl_2F_4$ isomers can be subjected to hydrogenolysis over a particulate catalyst of palladium on charcoal (which was intimately mixed with glass helices to prevent clogging) or over palladium on alumina, to mixtures of $C_2H_2F_4$ isomers. When using such catalysts, it is reported that when the organic starting material is CFC-114 the reaction product usually comprises a mixture of the two isomers of tetrafluoroethane. It is further disclosed that an alumina support is especially useful for the manufacture of 1,1,1,2-tetrafluoroethane (i.e., $CF_3CH_2F$ or HFC-134a) while an activated carbon support is especially useful for the manufacture of a mixture of HFC-134a and HFC-134. U.S. Pat. No. 4,319,060 discloses a process wherein CFC-114a contained in mixtures of CFC-114 and CFC-114a is selectively degraded to provide CFC-114 substantially free of CFC-114a. The process includes contacting, in the vapor phase, an organic feed composition containing a major amount of the 1,2-isomer and a minor amount of the 1,1-isomer with hydrogen in the presence of a hydrodechlorination catalyst.

It is well known that the hydrogenolysis of compounds such as $C_2Cl_2F_4$ to replace chlorine by hydrogen produces hydrogen chloride as a co-product and that loss of fluorine (e.g., to produce $C_2H_3F_3$) can produce HF as a by-product.

SUMMARY OF THE INVENTION

The present invention provides a process for the hydrogenolysis of a saturated acyclic starting material of the formula $C_nH_aX_bF_c$, wherein each X is selected from the group consisting of Cl and Br, n is an integer from 1 to 4, a is an integer from 0 to 3, b is an integer from 1 to 4 and c is an integer from 1 to 9. The process comprises reacting said starting material with hydrogen at an elevated temperature of about 300° C. or less in the presence of a catalyst containing a catalytically effective amount of palladium supported on trivalent chromium oxide and in the presence of an acid of the formula HZ where Z is selected from the group consisting of Cl, Br, F, and mixtures thereof, to produce a saturated acyclic product compound of the formula $C_nH_dX_eF_c$ wherein e is less than b and d+e equals a+b (and n and c are as above).

DETAILED DESCRIPTION

The catalysts suitable for the process of this invention comprise palladium and may optionally contain other components such as other Group VIII metals and rhenium. The palladium is supported on chromium oxide. The chromium oxide may support mixtures of palladium and other metals. Any source of chromium oxide is suitable, but chromium oxide prepared by the thermal decomposition of $(NH_4)_2Cr_2O_7$ is especially preferred. A procedure for the preparation of $Cr_2O_3$ by the thermal decomposition of $(NH_4)_2Cr_2O_7$ is disclosed in U.S. Pat. No. 5,036,036, the entire contents of which are incorporated herein by reference.

The acid HZ is at least partially produced during the reaction as the halogen X is removed from the starting material as a result of the hydrogenolysis. Accordingly, Z is ordinarily at least in part Cl and Br. Of note are embodiments where each X is Cl and Z is at least partially Cl. Also of note are embodiments where Z is partially F (e.g., the acid is a mixture of HCl and HF).

HF can be present, for example, as a result of rigorous hydrogenolysis wherein fluorine substituents of the starting material are partially replaced by hydrogen. HF can also be present by virtue of its presence in the reaction feed. For example, residual HF can be present from processes used to manufacture the $C_nH_aX_bF_c$ starting material. Of note in this regard are embodiments where said starting material is a component of an azeotrope of HF and said starting material, and starting material from said azeotrope is reacted with hydrogen in the presence of HF from said azeotrope.

Unlike alumina supports which are readily fluorinated, chromia fluorinates much more slowly under the same reaction conditions. Without wishing to be bound by theory, it is believed that because of the slower fluorination, chromia supports maintain their surface area longer than alumina supports; thereby enhancing catalyst life.

The palladium-containing material used to prepare the catalyst is preferably from a palladium salt (e.g., palladium chloride). The other metals which may be added to the catalyst include those from Group VIII (e.g., Pt, Ru, Rh or Ni) and Re. The metal may be added in the conventional manner (e.g., as a soluble salt of the metal).

The concentration of palladium supported on the chromium oxide support is typically within the range of from about 0.2% to about 5% by weight of the catalyst. The concentration of other Group VIII metals and/or rhenium is typically within the range of from 0% to about 3% by weight of the catalyst, but palladium is ordinarily at least about 60 percent by weight of the total supported metal.

The invention is applicable to the hydrogenolysis of halofluorocarbons and/or hydrohalofluorocarbons that contain one or more fluorine atoms in the molecule. Included are chlorofluorocarbons and hydrochlorofluorocarbons composed, respectively, of carbon, chlorine and fluorine, and of carbon, hydrogen, chlorine and fluorine. The halofluorocarbons and hydrohalofluorocarbons may contain 1 to 4 carbon atoms, and preferably have 1 to 3 carbon atoms. The halofluorocarbons and hydrohalofluorocarbons are saturated acyclic compounds represented by the empirical formula $C_nH_aX_bF_c$, wherein X is selected from Cl and Br, where n is an integer from 1 to 4, a is an integer from 0 to 3, b is an integer from 1 to 4, and c is an integer from 1 to 9 (i.e., the sum of a, b and c equals 2n plus 2). In a preferred embodiment the halofluorocarbons and/or hydrohalofluorocarbons are represented by the above empirical formula where n is 1 to 3, a is 0 to 3, b is 1 to 3 and c is 1 to 7. Of note are embodiments where n is 2 (e.g., $CCl_2FCF_3$ and $CClF_2CClF_2$). Other embodiments using catalysts described herein for the hydrogenolysis of $CF_3CCl_2CF_3$ to achieve $CF_3CHClCH_3$ with high selectivity are further described in U.S. patent application Ser. No. 08/351,927. Of note are embodiments wherein the mole ratio of hydrogen to C—X bonds (i.e., total carbon-chlorine and carbon-bromine bonds) in the starting material is at least about 1:1.

The present invention provides a process for the selective hydrogenolysis of an isomeric mixture containing $CCl_2FCF_3$ and $CClF_2CClF_2$ wherein $CCl_2FCF_3$ is less than about 10% of the $C_2Cl_2F_4$ isomer mixture. This embodiment comprises contacting a gaseous mixture containing this isomeric mixture and hydrogen in a ratio of $H_2:C_2Cl_2F_4$ of at least about 2:1 over the palladium-chromium oxide catalyst at a temperature lower than 150° C. and at a contact time of at least 10 seconds. The catalyst and operating conditions of this process allow for essentially the complete conversion of the $CCl_2FCF_3$ present in the isomer mixture (typically to $CF_3CHFCl$ and $CH_2FCF_3$ with minimal degradation to $CF_3CH_3$) while leaving the $CClF_2CClF_2$ present in the isomer mixture essentially unreacted. The products of the hydrogenolysis and the unreacted $CClF_2CClF_2$ can be recovered (e.g., by distillation).

The present invention further provides a process for the selective hydrogenolysis of $CF_3CHFCl$ to $CH_2FCF_3$. This embodiment comprises contacting a gaseous mixture comprising $CF_3CHFCl$ and hydrogen over the palladium-chromium oxide catalyst at a temperature greater than 150° C. The catalyst and operating conditions of this process allow for a very selective conversion of $CF_3CHFCl$ to $CH_2FCF_3$.

Additionally, the present invention also provides a process for the hydrogenolysis of $CCl_2FCF_3$ to $CF_3CHFCl$, $CH_2FCF_3$ and $CH_3CF_3$. This embodiment comprises contacting a gaseous mixture comprising $C_2Cl_2F_4$ having less than about 5% of $CClF_2CClF_2$ isomer (i.e., $CCl_2FCF_3$ is at least about 95% of the total $C_2Cl_2F_4$), and hydrogen over the palladium-chromium oxide catalyst at a temperature lower than 200° C. The catalyst and operating conditions of this process allow for a high yield of useful products of hydrogenolysis. The products $CF_3CHFCl$, $CH_2FCF_3$ and $CH_3CF_3$ can be recovered by conventional techniques such as distillation. The unreacted $CCl_2FCF_3$ as well as any $CHClFCF_3$ can be recycled.

Yet another embodiment of this invention is the provision of a process for the hydrogenolysis of $CClF_2CClF_2$ to $CHF_2CClF_2$ and $CHF_2CHF_2$ essentially without isomerization to products containing —$CF_3$ groups. This embodiment comprises contacting a gaseous mixture comprising $CClF_2CClF_2$ and hydrogen over the palladium-chromium oxide catalyst at a temperature greater than 165° C. When essentially pure $CClF_2CClF_2$ is used as the starting material, the products of the hydrogenolysis can be separated and $CHF_2CHF_2$ recovered as a pure product containing essentially no $CH_2FCF_3$. Also the $CHF_2CClF_2$ can be used as a product or recycled back to the reactor with additional $CClF_2CClF_2$.

The hydrogenolysis of the present invention is conducted at an elevated temperature. Ordinarily the temperature is about 300° C., or less, in order to minimize fluorination of the support. Preferably the temperature is at least about 50° C. Typically, advantageous reaction rates are achieved at operating temperatures of about 100° C., or more (e.g., at temperatures within the range of about 150° C. to 200° C.).

Pressure is not critical. Atmospheric and superatmospheric pressures are the most convenient and are therefore preferred.

Practice of the invention will become further apparent from the following non-limiting examples.

EXAMPLES

General Procedure for Catalyst Evaluation

A 6" (15 cm)×½" (1.3 cm) O. D. Hastelloy™ C nickel alloy reactor was charged with the catalyst (15 mL). The reactor contents were heated to a temperature of 150° C. for about an hour under nitrogen. The nitrogen flow was then stopped, and hydrogen was passed over the catalyst at 150° C. for about 3 hours and at 200° C. for an additional three hours. After this period, the reactor temperature was decreased to the desired operating temperature (° C.) for the hydrogenolysis reactions.

General Procedure for Product Analysis

The organic products leaving the reactor were analyzed on line using a gas chromatograph. The column consisted of a 20' (6.1 m)×⅛" (3.2 mm) s/s tube containing Krytox™ perfluorinated polyether on an inert support. Helium was used as the carrier gas. The organic product analyses are reported in mole %. Only a small portion of the total reactor effluent was sent to the gas chromatograph for organic product analysis. The bulk of the product stream (which also contained acids such as HCl and HF) was sent to a caustic scrubber for neutralization of the acids therein.

Catalyst Preparation

A solution containing palladium chloride (2.88 g), conc. hydrochloric acid (3 mL) and deionized water (100 mL) was prepared in a round-bottom flask. To this solution was added chromium oxide, $Cr_2O_3$, (98 g, 10×20 mesh (1.7×0.83 mm)) prepared by the pyrolysis of $(NH_4)_2Cr_2O_7$. The resulting slurry was gently stirred frequently and then dried in air at 150° C. for about 18 hours; followed by calcination in air for about 8 hours. Palladium on chromium oxide (96.7 g), containing about 2% palladium was isolated.

A sample of this 2% $Pd/Cr_2O_3$ was placed in the hydrogenolysis reactor and flushed with nitrogen at 150° C. for about one hour. The catalyst sample was then treated with hydrogen at 150° C. for about 3 hours and at 200° C. for about an additional 3 hours prior to use in Examples 1 to 4.

EXAMPLE 1

$CClF_2CClF_2 \rightarrow CHF_2CClF_2 + CHF_2CHF_2$

A feed containing 99.4% $CClF_2CClF_2$, 0.5% $CHClFCF_3$ and 0.1% $CHF_2CClF_2$, and hydrogen in a molar ratio of feed:hydrogen of 1:1 was passed over the 2% $Pd/Cr_2O_3$ (19 g, 15 mL) at a 30 second contact time and the temperatures shown in Table 1. The results of the hydrogenolysis are shown in Table 1. The HCl and small quantity of HF produced were scrubbed with caustic.

TABLE 1

| TEMP. °C. | $CH_4$ | $C_2H_6$ | 143a[1] | 134a[2] | 134[3] | 143[4] | 124a[5] | 124[6] | 114[7] |
|---|---|---|---|---|---|---|---|---|---|
| 175 | 0.0 | 0.1 | 0.0 | 0.2 | 0.3 | 0.0 | 18.9 | 0.2 | 80.4 |

TABLE 1-continued

| TEMP. °C. | CH$_4$ | C$_2$H$_6$ | 143a[1] | 134a[2] | 134[3] | 143[4] | 124a[5] | 124[6] | 114[7] |
|---|---|---|---|---|---|---|---|---|---|
| 200 | 0.2 | 0.2 | 0.0 | 0.3 | 1.7 | 0.1 | 44.5 | 0.2 | 52.6 |
| 225 | 0.4 | 1.0 | 0.1 | 0.2 | 5.6 | 0.1 | 64.2 | 0.1 | 28.3 |

[1]143a is CH$_3$CF$_3$,
[2]134a is CH$_2$FCF$_3$,
[3]143 is CHF$_2$CHF$_2$,
[4]124a is CH$_2$FCHF$_2$,
[5]124a is CHF$_2$CClF$_2$,
[6]124 is CHClFCF$_3$,
[7]114 is CClF$_2$CClF$_2$,

EXAMPLE 2

A feed containing 99.6% CCl$_2$FCF$_3$ and 0.4% CHClFCF$_3$, and hydrogen in a molar ratio of feed:hydrogen of 1:1 to 1:4 was passed over the 2% Pd/Cr$_2$O$_3$ (19 g, 15 mL) at a 15 to 30 second contact time (C.T.) and the temperatures shown in Table 2. The results of the hydrogenolysis are shown in Table 2. Inorganic acids such as HCl and HF produced in the reaction were scrubbed with caustic.

TABLE 2

| Temp. | H$_2$:114a | C. T. | 143a | 134a | 124 | 114a |
|---|---|---|---|---|---|---|
| 150 | 2:1 | 30 | 9.0 | 82.1 | 3.5 | 5.4 |
| 150 | 2:1 | 15 | 9.9 | 77.0 | 3.7 | 9.3 |
| 150 | 1:1 | 22 | 5.0 | 40.1 | 2.0 | 52.7 |
| 140 | 2:1 | 15 | 6.9 | 71.9 | 4.5 | 16.7 |
| 130 | 2:1 | 15 | 4.2 | 60.7 | 4.3 | 30.7 |
| 125 | 2:1 | 30 | 5.1 | 64.4 | 4.5 | 26.0 |
| 125 | 4:1 | 30 | 5.0 | 77.4 | 6.5 | 11.1 |
| 125 | 4:1 | 15 | 3.8 | 66.8 | 6.0 | 23.3 |
| 120 | 2:1 | 15 | 2.5 | 44.5 | 3.8 | 49.3 |
| 110 | 2:1 | 15 | 1.4 | 29.4 | 2.9 | 66.3 |
| 100 | 4:1 | 30 | 1.8 | 34.0 | 4.0 | 60.1 |
| 100 | 2:1 | 30 | 1.5 | 25.2 | 2.8 | 70.5 |
| 100 | 2:1 | 15 | 0.8 | 17.3 | 2.1 | 79.8 |

EXAMPLE 3

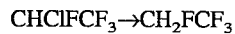

A feed containing 99.9% CHClFCF$_3$ and hydrogen in a molar ratio of feed:hydrogen of 1:1 was passed over the 2% Pd/Cr$_2$O$_3$ (19 g, 15 mL) at a 20 to 60 second contact time and the temperatures shown in Table 3. The results of the hydrogenolysis are shown in Table 3. The HCl and small quantity of HF produced in the reactor were scrubbed with caustic.

TABLE 3

| Temp. | C. T. | 143a | 134a | 124 |
|---|---|---|---|---|
| 150 | 15 | 0.0 | 2.2 | 97.8 |
| 175 | 15 | 0.0 | 7.6 | 92.3 |
| 200 | 15 | 0.1 | 23.0 | 76.8 |
| 200 | 22 | 0.1 | 26.9 | 72.9 |
| 200 | 30 | 0.1 | 30.7 | 69.1 |
| 200 | 45 | 0.1 | 37.1 | 62.6 |

EXAMPLE 4

C$_2$C$_2$F$_4$ Hydrogenolysis

A feed containing 89.8% CClF$_2$CClF$_2$ and 10.1% CCl$_2$FCF$_3$, and hydrogen in a molar ratio of feed:hydrogen of 2:1 was passed over the 2% Pd/Cr$_2$O$_3$ (19 g, 15 mL) at a 15 second contact time and the temperatures shown in Table 4. The results of the hydrogenolysis are shown in Table 4. Inorganic acids produced during the reaction were neutralized with caustic.

TABLE 4

| Temp. | 143a | 134a | 124a | 124 | 114 | 114a |
|---|---|---|---|---|---|---|
| 150 | 0.8 | 9.0 | 1.4 | 0.9 | 88.0 | 0.0 |
| 125 | 0.6 | 8.3 | 0.2 | 0.9 | 89.0 | 1.1 |
| 100 | 0.3 | 3.8 | 0.1 | 0.5 | 89.3 | 6.0 |

What is claimed is:

1. A process for the hydrogenolysis of a saturated acyclic starting material of the formula C$_n$H$_a$X$_b$F$_c$, wherein each X is selected from the group consisting of Cl and Br, n is an integer from 1 to 4, a is an integer from 0 to 3, b is an integer from 1 to 4 and c is an integer from 1 to 9, comprising:

reacting said starting material with hydrogen at an elevated temperature of about 300° C. or less in the presence of a catalyst containing a catalytically effective amount of palladium supported on trivalent chromium oxide and in the presence of an acid of the formula HZ where Z is selected from the group consisting of Cl, Br, F and mixtures thereof, to produce a product compound of the formula C$_n$H$_d$X$_e$F$_c$ where e is less than b and d+e equals a+b.

2. The process of claim 1 wherein each X is Cl and Z is at least partially Cl.

3. The process of claim 1 wherein HF is present in the reaction feed.

4. The process of claim 1 wherein the concentration of palladium supported on chromium oxide is within the range of from about 0.2% to about 5% by weight of the catalyst.

5. The process of claim 1 wherein the starting material is CCl$_2$FCF$_3$.

6. The process of claim 1 wherein the starting material is CClF$_2$CClF$_2$.

7. The process of claim 1 wherein a gaseous mixture containing (a) an isomeric mixture of CCl$_2$FCF$_3$ and CClF$_2$CClF$_2$ wherein CCl$_2$FCF$_3$ is less than about 10% of the C$_2$Cl$_2$F$_4$ content and (b) hydrogen, is contacted over said catalyst at a temperature lower than 150° C. and a contact time of at least 10 seconds; wherein there is essentially complete conversion of the CCl$_2$FCF$_3$ present in the isomer mixture while the CCl$_2$FCCl$_2$F present in the isomer mixture is left essentially unreacted.

8. The process of claim 1 wherein CF$_3$CHClF is converted to CH$_2$FCF$_3$ at a temperature greater than 150° C.

9. The process of claim 1 wherein a gaseous mixture comprising C$_2$Cl$_2$F4 having less than about 5% CClF$_2$CClF$_2$ isomer and hydrogen and contacted over said catalyst at a temperature lower than 200° C. to produce $CF_3CHFCl$, $CH_2FCF_3$ and $CH_3CF_3$.

10. The process of claim 1 wherein $CClF_2CClF_2$ is converted to $CHF_2CClF_2$ and $CHF_2CHF_2$ at a temperature greater than 165° C. essentially without isomerization to products containing —$CF_3$ groups.

* * * * *